US 6,484,183 B1

(12) United States Patent
Balaban et al.

(10) Patent No.: US 6,484,183 B1
(45) Date of Patent: Nov. 19, 2002

(54) METHOD AND SYSTEM FOR PROVIDING A POLYMORPHISM DATABASE

(75) Inventors: David J. Balaban, San Rafael; Joyti Baid; Anthony Berno, both of San Jose, all of CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 09/122,169

(22) Filed: Jul. 24, 1998

Related U.S. Application Data

(60) Provisional application No. 60/069,436, filed on Dec. 11, 1997, provisional application No. 60/069,198, filed on Dec. 11, 1997, and provisional application No. 60/053,842, filed on Jul. 25, 1997.

(51) Int. Cl.$^7$ .............................................. G06F 17/30
(52) U.S. Cl. ...................................... 707/104.1; 707/10
(58) Field of Search ............................. 707/4, 10, 100, 707/101, 103, 104; 435/325

(56) References Cited

U.S. PATENT DOCUMENTS

| | | | | |
|---|---|---|---|---|
| 5,819,282 A | * | 10/1998 | Hooper et al. ............... | 707/103 |
| 5,843,669 A | * | 12/1998 | Kaiser et al. .................. | 435/6 |
| 5,843,767 A | | 12/1998 | Beattie ........................ | 435/287 |
| 5,991,766 A | * | 11/1999 | Sadiq et al. ................. | 707/103 |
| 6,032,151 A | * | 2/2000 | Arnold et al. ............... | 707/103 |
| 6,140,054 A | * | 10/2000 | Wittwer et al. ................ | 435/6 |

FOREIGN PATENT DOCUMENTS

EP       0 848 067       6/1998

OTHER PUBLICATIONS

IntelliGenetics Suite (TM), Release 5.4, Advanced Training Manual, Jan. 1993, published by IntelliGenetics, Inc., 700 East El Camino Real, Mountain View, California 94040, USA, pp. (1–6)—(1–19) and (2–9)—(2–14), see entire document.

Okubo et al., "Large Scale cDNA Sequencing for Analysis of Quantitative and Qualitative Aspects of Gene Expression", *Nature Genetics*, 2(3):173–179 (1993).

Zhao et al., "High–density cDNA filter analysis: a novel approach for large–scale, quantitative analysis of gene expression," *Gene*, 156:207–213 (1995).

U.S. patent application Ser. No. 08/531,137, Chee et al., filed Oct. 16, 1995.

(List continued on next page.)

*Primary Examiner*—Diane D. Mizrahi
(74) *Attorney, Agent, or Firm*—Townsend and Townsend and Crew, LLP

(57) ABSTRACT

Systems and methods for organizing information relating to study of polymorphisms. A database model is provided which interrelates information about one or more of, e.g, subjects from whom samples are extracted, primers used in extracting the DNA from the subjects, about the samples themselves, about experiments done on samples, about particular oligonucleotide probe arrays used to perform experiments, about analysis procedures performed on the samples, and about analysis results. The model is readily translatable into database languages such as SQL. The database model scales to permit storage of information about large numbers of subjects, samples, experiments, chips, etc.

19 Claims, 16 Drawing Sheets

OTHER PUBLICATIONS

Adams et al., "Complementary DNA Sequencing: Expressed Sequence Tags and Human Genome Project", *Science*, 252(5013):1651–1656 (1991).

Frickett et al., "Development Of A Database For Nucleotide Sequences", *Mathematical Methods for DNA Sequences*, CRC Press, Ed. Waterman, pp. 2–34 (1989).

Hara et al., "Subtractive cDNA Cloning Using Oligo(dT)$_{30}$–Latex And PCR: Isolation Of cDNA Clones Specific To Undifferentiated Human Embryonal Carcinoma Cells", *Nucleic Acids Res.*, 19(25):7097–7104 (1991).

Khan et al., "Single Pass Sequencing And Physical And Genetic Mapping Of Human Brain cDNAs", *Nat Genet.*, 2(3):180–185 (1992).

Matsubara et al., "Identification Of New Genes By Systematic Analysis Of cDNAs And Database Construction", *Curr. Opin. Biotechnol.*, 4(6):672–677 (1993).

Allee, Chip, "Data Management for Automated Drug Discovery Laboratories," Laboratory Robotics and Automation, Aug. 21, 1996, pp. 307–310.

Kerlavage, Anthony R, et al., "Data Management and Analysis for High–Throughput DNA Sequencing Projects," IEEE Engineering In Medicine and Biology, Nov./Dec. 1995, pp. 710–717.

"Introduction to Database Systems –Chapter 4, An Overview of DB2,"1990, pp. 111–116.

* cited by examiner

METHOD AND SYSTEM FOR PROVIDING A POLYMORPHISM DATABASE

CROSS-REFERENCE TO RELATED APPLICATIONS

The present application claims priority from U.S. Prov. App. No. 60/053,842 filed Jul. 25, 1997, entitled COMPREHENSIVE BIO-INFORMATICS DATABASE, from U.S. Prov. App. No. 60/069,198 filed on Dec. 11, 1997, entitled COMPREHENSIVE DATABASE FOR BIOINFORMATICS, and from U.S. Prov. App. No. 60/069,436, entitled GENE EXPRESSION AND EVALUATION SYSTEM, filed on Dec. 11, 1997. The contents of all three provisional applications are herein incorporated by reference.

The subject matter of the present application is related to the subject matter of the following three co-assigned applications filed on the same day as the present application. GENE EXPRESSION AND EVALUATION SYSTEM pending U.S. application Ser. No. 09/122,434, METHOD AND APPARATUS FOR PROVIDING A BIOINFORMATICS DATABASE U.S. application Ser. No. 09/122,167, and U.S. Pat. No. 6,229,911, METHOD AND SYSTEM FOR PROVIDING A PROBE ARRAY CHIP DESIGN DATABASE U.S. application Ser. No. 09/122,304 and now U.S. Pat. No. 6,188,783. The contents of these three applications are herein incorporated by reference.

BACKGROUND OF THE INVENTION

The present invention relates to the collection and storage of information pertaining to chips for processing biological samples and thereby identifying polymorphisms.

The genomes of all organisms undergo spontaneous mutation in the course of their continuing evolution generating variant forms of progenitor sequences (Gusella, *Ann. Rev. Biochem.* 55, 831–854 (1986)). The variant form may confer an evolutionary advantage or disadvantage relative to a progenitor form or may be neutral. In some instances, a variant form confers a lethal disadvantage and is not transmitted to subsequent generations of the organism. In other instances, a variant form confers an evolutionary advantage to the species and is eventually incorporated into the DNA of many or most members of the species and effectively becomes the progenitor form. In many instances, both progenitor and variant form(s) survive and co-exist in a species population. The coexistence of multiple forms of a sequence gives rise to polymorphisms.

Despite the increased amount of nucleotide sequence data being generated in recent years, only a minute proportion of the total repository of polymorphisms in humans and other organisms has so far been identified. The paucity of polymorphisms hitherto identified is due to the large amount of work required for their detection by conventional methods. For example, a conventional approach to identifying polymorphisms might be to sequence the same stretch of oligonucleotides in a population of individuals by dideoxy sequencing. In this type of approach, the amount of work increases in proportion to both the length of sequence and the number of individuals in a population and becomes .impractical for large stretches of DNA or large numbers of persons.

Devices and computer systems for forming and using arrays of materials on a substrate have been developed. These devices and systems have been used for identifying polymorphisms. For example, PCT application WO92/10588, incorporated herein by reference for all purposes, describes techniques for sequencing or sequence checking nucleic acids and other materials. Arrays for performing these operations may be formed in arrays according to the methods of, for example, the pioneering techniques disclosed in U.S. Pat. No. 5,143,854 and U.S. Pat. No. 5,571,639, both incorporated herein by reference for all purposes.

According to one aspect of the techniques described therein, an array of nucleic acid probes is fabricated at known locations on a chip or substrate. A fluorescently labeled nucleic acid is then brought into contact with the chip and a scanner generates an image file indicating the locations where the labeled nucleic acids bound to the chip. Based upon the identities of the probes at these locations, it becomes possible to extract information such as the identity of polymorphic forms in of DNA or RNA. Such systems have been used to form, for example, arrays of DNA that may be used to study and detect mutations relevant to cystic fibrosis, the P53 gene (relevant to certain cancers), HIV, and other genetic characteristics.

It would be highly useful to apply such arrays to the study of polymorphisms on a large scale. For example, it would be useful to conduct large scale studies on the correlation between certain polymorphisms and individual characteristics such as susceptibility to diseases and effectiveness of drug treatments. To achieve these benefits, it is contemplated that the operations of chip design, construction, sample preparation, and analysis will occur on a very large scale. The quantity of information related to each of these steps to store and correlate is vast. For large scale polymorphism studies, it will be necessary to store this information in a way to facilitate later advantageous querying and retrieval. What is needed is a system and method suitable for storing and organizing large quantities of information used in conjunction with polymorphism studies.

SUMMARY OF THE INVENTION

The present invention provides systems and methods for organizing information relating to study of polymorphisms. A database model is provided which interrelates information about one or more of, e.g, subjects from whom samples are extracted, primers used in extracting the DNA from the subjects, about the samples themselves, about experiments done on samples, about particular oligonucleotide probe arrays used to perform experiments, about analysis procedures performed on the samples, and about analysis results. The model is readily translatable into database languages such as SQL. The database model scales to permit storage of information about large numbers of subjects, samples, experiments, chips, etc.

Applications include linkage studies to determine resistance to drugs, susceptibility to diseases, and study of every characteristic of humans and other organisms that is related genetic variability. Another application of a database constructed according to this model is quality control of the various steps of performing a polymorphism study. By preserving information about every step of a polymorphism study, one can assess the reliability of the results or use the preserved information as feedback to improve procedures.

A further understanding of the nature and advantages of the inventions herein may be realized by reference to the remaining portions of the specification and the attached drawings.

DESCRIPTION OF SPECIFIC EMBODIMENTS

Investigation of Polymorphisms

A. Preparation of Samples

Figure 1:
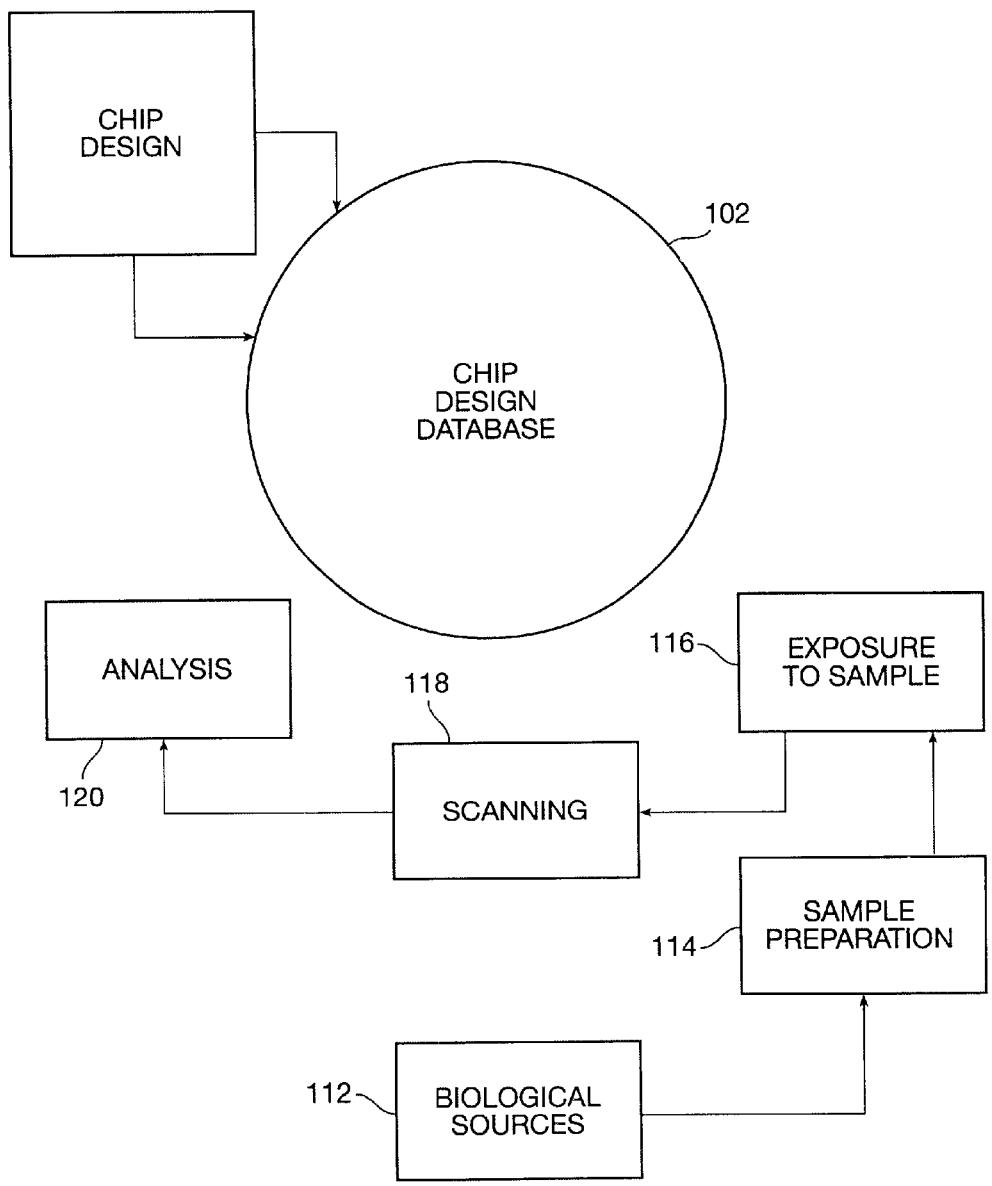
FIG. 1 illustrates an overall system and process for forming and analyzing arrays of biological materials such as DNA or RNA.

Polymorphisms are detected in a target nucleic acid from an individual being analyzed. For assay of genomic DNA, virtually any biological sample (other than pure red blood cells) is suitable. For example, convenient tissue samples include whole blood, semen, saliva, tears, urine, fecal material, sweat, buccal, skin and hair. For assay of cDNA or mRNA, the tissue sample must be obtained from an organ in which the target nucleic acid is expressed. For example, if the target nucleic acid is a cytochrome P450, the liver is a suitable source.

Many of the methods described below require amplification of DNA from target samples. This can be accomplished by e.g., PCR. See generally *PCR Technology: Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Mattila et al., *Nucleic Acids Res.* 19, 4967 (1991); Eckert et al., *PCR Methods and Applications* 1, 17 (1991); PCR (eds. McPherson et al., IRL Press, Oxford); and U.S. Pat. No. 4,683,202 (each of which is incorporated by reference for all purposes).

Other suitable amplification methods include the ligase chain reaction (LCR) (see Wu and Wallace, *Genomics* 4, 560 (1989), Landegren et al., *Science* 241, 1077 (1988), transcription amplification (Kwoh et al., *Proc. Natl. Acad. Sci. USA* 86, 1173 (1989)), and self-sustained sequence replication (Guatelli et al., *Proc. Nat. Acad. Sci. USA*, 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

B. Detection of Polymorphisms in Target DNA

There are two distinct types of analysis depending whether a polymorphism in question has already been characterized. The first type of analysis is sometimes referred to as de novo characterization. This analysis compares target sequences in different individuals to identify points of variation, i.e., polymorphic sites. By analyzing groups of individuals representing the greatest ethnic diversity among humans and greatest breed and species variety in plants and animals, patterns characteristic of the most common alleles/haplotypes of the locus can be identified, and the frequencies of such populations in the population determined. Additional allelic frequencies can be determined for subpopulations characterized by criteria such as geography, race, or gender. The second type of analysis is determining which form(s) of a characterized polymorphism are present in individuals under test. There are a variety of suitable procedures, which are discussed in turn.

1. Allele-Specific Probes

The design and use of allele-specific probes for analyzing polymorphisms is described by e.g., Saiki et al., *Nature* 324,163–166 (1986); Dattagupta, EP 235,726, Saiki, WO 89/11548. Allele-specific probes can be designed that hybridize to a segment of target DNA from one individual but do not hybridize to the corresponding segment from another individual due to the presence of different polymorphic forms in the respective segments from the two individuals. Hybridization conditions should be sufficiently stringent that there is a significant difference in hybridization intensity between alleles, and preferably an essentially binary response, whereby a probe hybridizes to only one of the alleles. Some probes are designed to hybridize to a segment of target DNA such that the polymorphic site aligns with a central position (e.g., in a 15 mer at the 7 position; in a 16 mer, at either the 8 or 9 position) of the probe. This design of probe achieves good discrimination in hybridization between different allelic forms.

Allele-specific probes are often used in pairs, one member of a pair showing a perfect match to a reference form of a target sequence and the other member showing a perfect match to a variant form. Several pairs of probes can then be immobilized on the same support for simultaneous analysis of multiple polymorphisms within the same target sequence.

2. Tiling Arrays

The polymorphisms can also be identified by hybridization to nucleic acid arrays, some example of which are described by WO 95/11995 (incorporated by reference in its entirety for all purposes). WO 95/11995 also describes subarrays that are optimized for detection of a variant forms of a precharacterized polymorphism. Such a subarray contains probes designed to be complementary to a second reference sequence, which is an allelic variant of the first reference sequence. The second group of probes is designed by the same principles as described in the Examples except that the probes exhibit complementarily to the second reference sequence. The inclusion of a second group (or further groups) can be particular useful for analyzing short subsequences of the primary reference sequence in which multiple mutations are expected to occur within a short distance commensurate with the length of the probes (i.e., two or more mutations within 9 to 21 bases).

3. Allele-Specific Primers

An allele-specific primer hybridizes to a site on target DNA overlapping a polymorphism and only primes amplification of an allelic form to which the primer exhibits perfect complementarily. See Gibbs, *Nucleic Acid Res.* 17, 2427–2448 (1989). This primer is used in conjunction with a second primer which hybridizes at a distal site. Amplification proceeds from the two primers leading to a detectable product signifying the particular allelic form is present. A control is usually performed with a second pair of primers, one of which shows a single base mismatch at the polymorphic site and the other of which exhibits perfect complementarily to a distal site. The single-base mismatch prevents amplification and no detectable product is formed. The method works best when the mismatch is included in the 3'-most position of the oligonucleotide aligned with the polymorphism because this position is most destabilizing to elongation from the primer. See, e.g., WO 93/22456.

4. Direct-Sequencing

The direct analysis of the sequence of polymorphisms of the present invention can be accomplished using either the dideoxy chain termination method or the Maxam Gilbert method (see Sambrook et al., *Molecular Cloning, A Laboratory Manual* (2nd Ed., CSHP, New York 1989); Zyskind et al., *Recombinant DNA Laboratory Manual*, (Acad. Press, 1988)).

5. Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution. Erlich, ed., *PCR Technology, Principles and Applications for DNA Amplification*, (W. H. Freeman and Co, New York, 1992), Chapter 7.

6. Single-Strand Conformation Polymorphism Analysis

Alleles of target sequences can be differentiated using single-strand conformation polymorphism analysis, which identifies base differences by alteration in electrophoretic migration of single stranded PCR products, as described in Orita et al., Proc. Nat. Acad. Sci. 86, 2766–2770 (1989). Amplified PCR products can be generated as described above, and heated or otherwise denatured, to form single stranded amplification products. Single-stranded nucleic acids may refold or form secondary structures which are partially dependent on the base sequence. The different electrophoretic mobilities of single-stranded amplification products can be related to base-sequence difference between alleles of target sequences.

Biological Material Analysis System

One embodiment of the present invention operates in the context of a system for analyzing biological or other materials using arrays that themselves include probes that may be made of biological materials such as RNA or DNA. The VLSIPS™ and GeneChip™ technologies provide methods of making and using very large arrays of polymers, such as nucleic acids, on chips. See U.S. Pat. No. 5,143,854 and PCT Patent Publication Nos. WO 90/15070 and 92/10092, each of which is hereby incorporated by reference for all purposes. Nucleic acid probes on the chip are used to detect complementary nucleic acid sequences in a sample nucleic acid of interest (the "target" nucleic acid).

FIG. 1 illustrates an overall system 100 for forming and analyzing arrays of biological materials such as RNA or DNA. A part of system 100 is a polymorphism database 102. Polymorphism database 102 includes information about, e.g., biological sources, preparation of samples, design of arrays, raw data obtained from applying experiments to chips, analysis procedures applied, and analysis results, etc. Polymorphism database 102 facilitates large scale study of polymorphisms.

A chip design system 104 is used to design arrays of polymers such as biological polymers such as RNA or DNA. Chip design system 104 may be, for example, an appropriately programmed Sun Workstation or personal computer or workstation, such as an IBM PC equivalent, including appropriate memory and a CPU. Chip design system 104 obtains inputs from a user regarding chip design objectives including polymorphisms of interest, and other inputs regarding the desired features of the array. Optionally, chip design system 104 from external databases such as GenBank. The output of chip design system 104 is a set of chip design computer files in the form of, for example, a switch matrix, as described in PCT application WO 92/10092, and other associated computer files. The chip design computer files form a part of polymorphism database 102. Systems for designing chips for study of polymorphisms are disclosed in U.S. Pat. No. 5,571,639 and in PCT application WO 95/11995, the contents of which are herein incorporated by reference.

The chip design files are input to a mask design system (not shown) that designs the lithographic masks used in the fabrication of arrays of molecules such as DNA. The mask design system designs the lithographic masks used in the fabrication of probe arrays. The mask design system generates mask design files that are then used by a mask construction system (not shown) to construct masks or other synthesis patterns such as chrome-on-glass masks for use in the fabrication of polymer arrays.

The masks are used in a synthesis system (not shown). The synthesis system includes the necessary hardware and software used to fabricate arrays of polymers on a substrate or chip. The synthesis system includes a light source and a chemical flow cell on which the substrate or chip is placed. A mask is placed between the light source and the substrate/chip, and the two are translated relative to each other at appropriate times for deprotection of selected regions of the chip. Selected chemical reagents are directed through the flow cell for coupling to deprotected regions, as well as for washing and other operations. The substrates fabricated by the synthesis system are optionally diced into smaller chips. The output of the synthesis system is a chip ready for application of a target sample.

Information about the mask design, mask construction, and probe array synthesis is presented by way of background. A biological source 112 is, for example, tissue from a plant or animal. Various processing steps are applied to material from biological source 112 by a sample preparation system 114. Operation of sample preparation system 114 in the context of a polymorphism study is discussed below in further detail.

The prepared samples include nucleic acid sequences such as DNA. When the sample is applied to the chip by a sample exposure system 116, the nucleic acids may or may not bond to the probes. The nucleic acids can be tagged with fluoroscein labels to determine which probes have bonded to nucleotide sequences from the sample. The prepared samples will be placed in a scanning system 118. Scanning system 118 includes a detection device such as a confocal microscope or CCD (charge-coupled device) that is used to detect the location where labeled receptors have bound to the substrate. The output of scanning system 118 is an image file(s) indicating, in the case of fluoroscein labeled receptor, the fluorescence intensity (photon counts or other related measurements, such as voltage) as a function of position on the substrate. These image files may also form a part of polymorphism database 102. Since higher photon counts will be observed where the labeled nucleic acid(s) has bound more strongly to the array of probes, and since the monomer sequence of the probes on the substrate is known as a function of position, it becomes possible to analyze the sequence(s) of the nucleic acid(s) that are complementary to the probes.

The image files and the design of the chips are input to an analysis system 120 that, e.g., calls bases. Such analysis techniques are described in EPO Pub. No. 0717113A, the contents of which are herein incorporated by reference. Chip design system 104, analysis system 120 and control portions of exposure system 116, sample preparation system 114, and scanning system 118 may be appropriately programmed computers such as a Sun workstation or IBM-compatible PC. An independent computer for each system may perform the computer-implemented functions of these systems or one computer may combine the computerized functions of two or more systems. One or more computers may maintain chip design database 102 independent of the computers operating the systems of FIG. 1 or chip design database 102 may be fully or partially maintained by these computers.

Figure 2A:
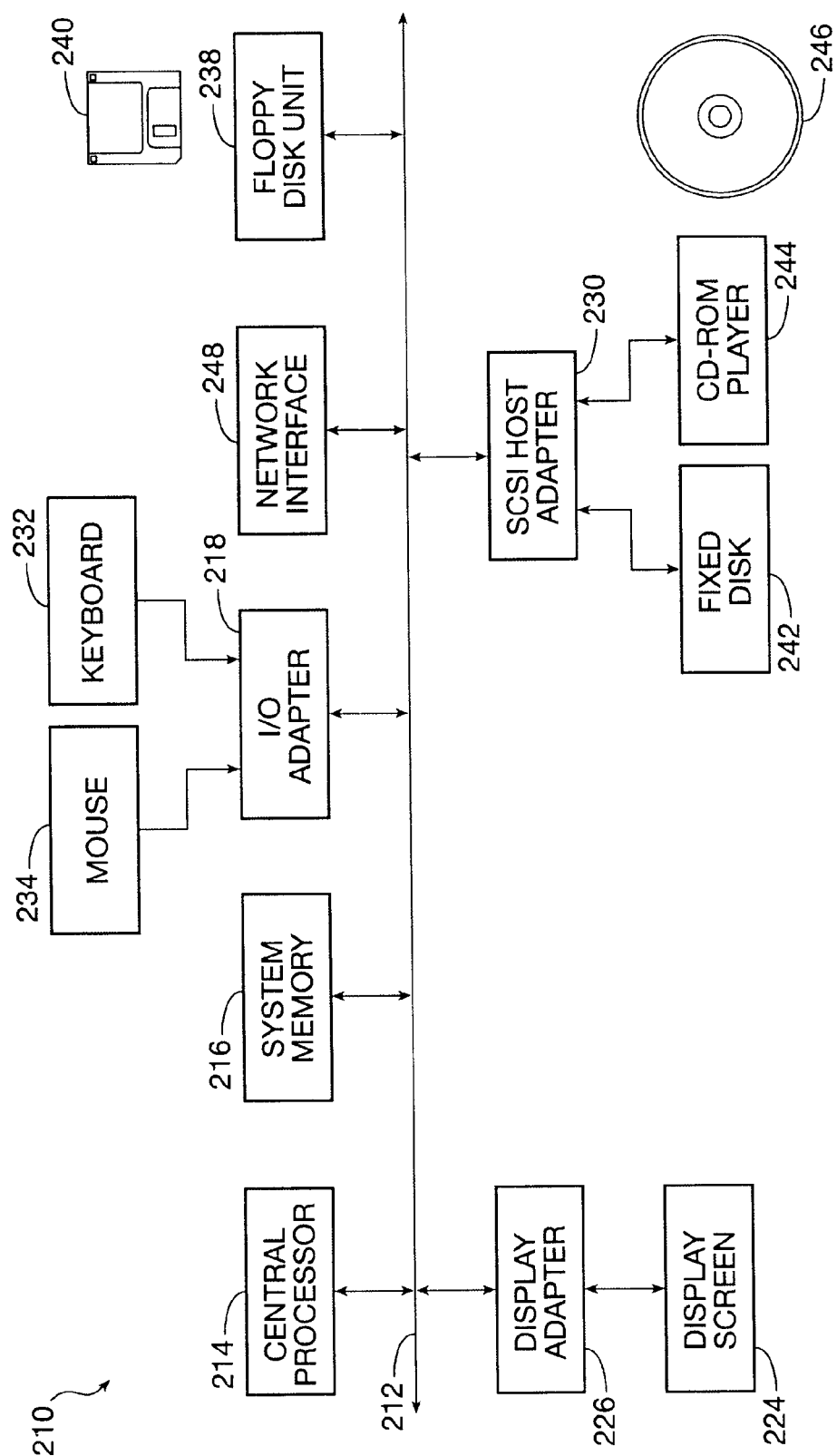
FIG. 2A illustrates a computer system suitable for use in conjunction with the overall system of FIG. 1.

FIG. 2A depicts a block diagram of a host computer system 10 suitable for implementing the present invention.

Host computer system 210 includes a bus 212 which interconnects major subsystems such as a central processor 214, a system memory 216 (typically RAM), an input/output (I/O) adapter 218, an external device such as a display screen 224 via a display adapter 226, a keyboard 232 and a mouse 234 via an I/O adapter 218, a SCSI host adapter 236, and a floppy disk drive 238 operative to receive a floppy disk 240. SCSI host adapter 236 may act as a storage interface to a fixed disk drive 242 or a CD-ROM player 244 operative to receive a CD-ROM 246. Fixed disk 244 may be a part of host computer system 210 or may be separate and accessed through other interface systems. A network interface 248 may provide a direct connection to a remote server via a telephone link or to the Internet. Network interface 248 may also connect to a local area network (LAN) or other network interconnecting many computer systems. Many other devices or subsystems (not shown) may be connected in a similar manner.

Also, it is not necessary for all of the devices shown in FIG. 2A to be present to practice the present invention, as discussed below. The devices and subsystems may be interconnected in different ways from that shown in FIG. 2A. The operation of a computer system such as that shown in FIG. 2A is readily known in the art and is not discussed in detail in this application. Code to implement the present invention, may be operably disposed or stored in computer-readable storage media such as system memory 216, fixed disk 242, CD-ROM 246, or floppy disk 240.

Figure 2B:
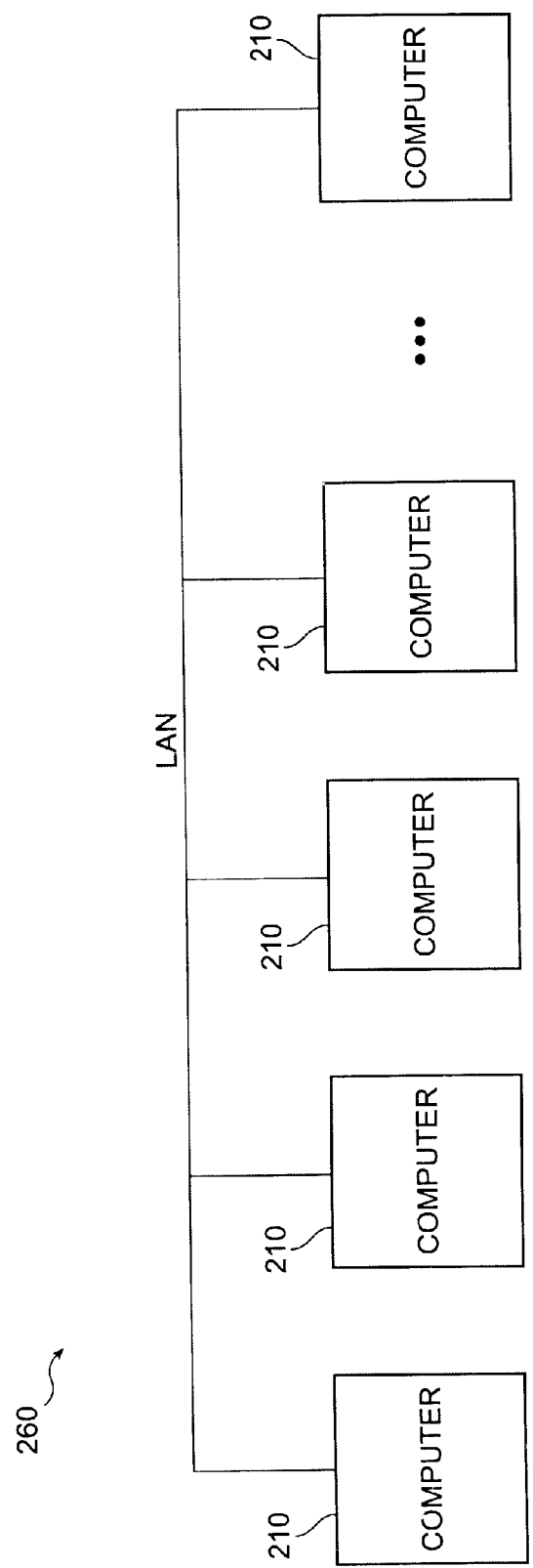
FIG. 2B illustrates a computer network suitable for use in conjunction with the overall system of FIG. 1.

FIG. 2B depicts a network 260 interconnecting multiple computer systems 210. Network 260 may be a local area network (LAN), wide area network (WAN), etc. Bioinformatics database 102 and the computer-related operations of the other elements of FIG. 2B may be divided amongst computer systems 210 in any way with network 260 being used to conimunicate information among the various computers. Portable storage media such as floppy disks may be used to carry information between computers instead of network 260.

Overall Description of Database

Polymorphism database 102 is preferably a relational database with a complex internal structure. The structure and contents of chip design database 102 will be described with reference to a logical model depicted in FIGS. 4A–4H that describes the contents of tables of the database as well as interrelationships among the tables. A visual depiction of this model will be an Entity Relationship Diagram (ERD) which includes entities, relationships, and attributes. A detailed discussion of ERDs is found in "ERwin version 3.0 Methods Guide" available from Logic Works, Inc. of Princeton, N.J., the contents of which are herein incorporated by reference. Those of skill in the art will appreciate that automated tools such as Developer 2000 available from Oracle will convert the ERD from FIGS. 4A–4H directly into executable code such as SQL code for creating and operating the database.

Figure 3:
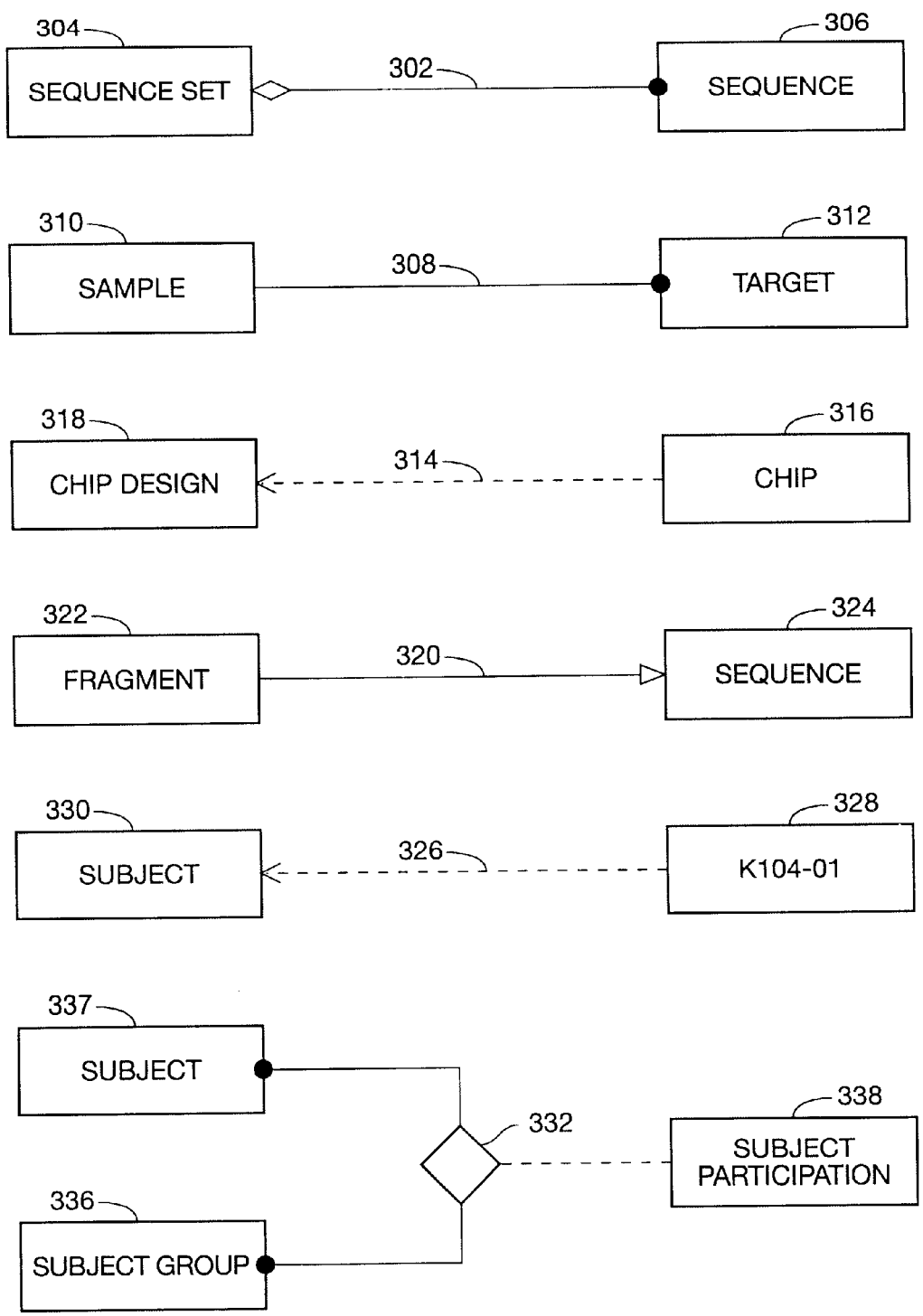
FIG. 3 illustrates a key for interpreting a database model.

FIG. 3 is a key to the ERD that will be used to describe the contents of chip design database 102. A representative table 302 includes one or more key attributes 304 and one or more non-key attributes 306. Representative table 302 includes one or more records where each record includes fields corresponding to the listed attributes. The contents of the key fields taken together identify an individual record. In the ERD, each table is represented by a rectangle divided by a horizontal line. The fields or attributes above the line are key while the fields or attributes below the line are non-key.

An identifying relationship 308 signifies that the key attribute of a parent table 310 is also a key attribute of a child table 312. A non-identifying relationship 314 signifies that the key attribute of a parent table 316 is also a non-key attribute of a child table 318. Where (FK) appears in parenthesis, it indicates that an attribute of one table is a key attribute of another table. Both the depicted non-identifying and identifying relationship are one to one-or-more relationships where one record in the parent table corresponds to one or more records in the child table. An alternative non-identifying relationship 324 is a one to zero-or-more relationship where one record in a parent table 320 corresponds to zero or more records in a child table 322.

Database Model

FIGS. 4A–4H are entity relationship diagrams (ERDs) showing elements of polymorphism database 102 according to one embodiment of the present invention. Each rectangle in the diagram corresponds to a table in database 102. First, the relationships and general contents of the various tables will be described.

The interrelationships and general contents of the tables of database 102 will be described first. Then a chart will be presented listing and describing all of the fields of the various tables.

Figure 4A:
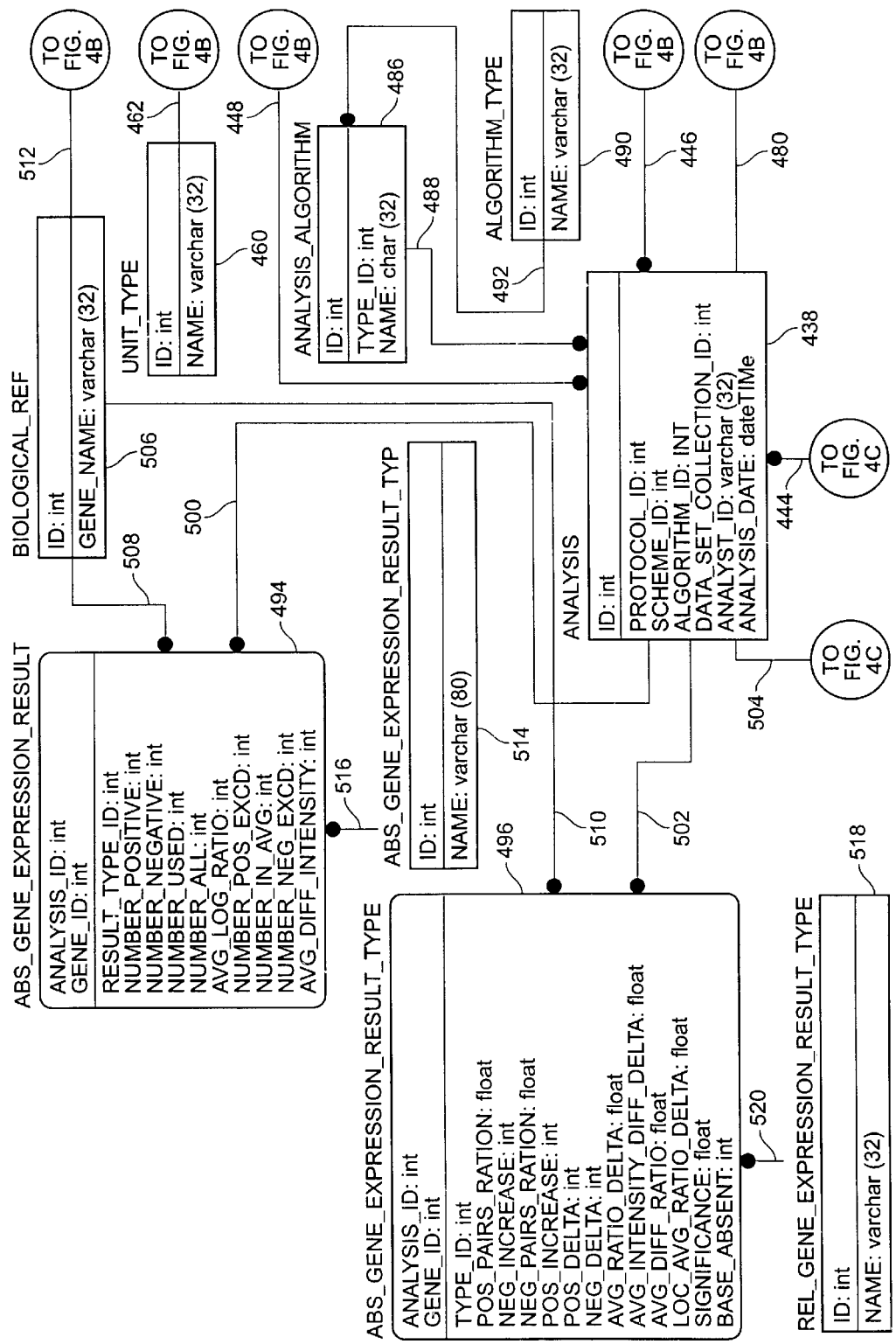
FIGS. 4A–4H illustrate a database model for maintaining information for the system and process of FIG. 1 according to one embodiment of the present invention.

FIG. 4A illustrates core elements of database 102 according to one embodiment of the present invention. A subject table 402 lists organisms from which samples have been extracted for polymorphism analysis or other tissue sources. Samples may also be obtained from tissue collections not associated with any one identified organism. Information stored within subject table 402 includes the name, gender, family, position with family, (e.g., father, mother, etc.), and ethnic group. For human subjects, the name and family will preferably be represented in coded form to assure privacy. Associated with each subject is a species as listed in a species table 404. Also, a relationship may be defined among subjects in a subject relationship table 406 which includes records corresponding to related subjects. These relationships may be father-mother, sibling, twins, etc. Subjects may be part of a group that is being studied, e.g., a group with a congenital disease, or a toxic reaction to a particular drug. The groups are listed in a subject group table 408. Participation of subjects in groups is defined by a subject participation table 410 which lists all group memberships.

Samples and their attributes are listed in a sample table 412. Each sample has an associated sample type. The sample types are listed in a sample type table 414. Possible sample types include blood, urine, etc. Companies or institutions that provide samples are listed in a sample source table 416.

Database 102 provides an item table 418 that includes records for items. There are various types of items that correspond to different stages of the sample preparation process. An "item derivation" transforms an item of one type into an item of another type. The following table lists various item types and item derivation types for a representative embodiment.

| Item Type | Derived from | by Item Derivation Type |
|---|---|---|
| Sample | other samples | pooling |
| Sample | other sample | splitting |
| Extracted DNA | Sarnple | DNA Extraction |

-continued

| Item Type | Derived from | by Item Derivation Type |
|---|---|---|
| Target (Sequences of interest amplified) | Extracted DNA | PCR |
| Fluorescently Labeled Target | Target | Labeling |
| Hybridized Chip | Labeled Target | Hybridization (application of target to chip) |
| Stained Hybridized Chip | Hybridized Chip | Staining |

Item derivations are listed in an item derivation table 420. It should be noted that derivations need not produce a change between item types. Each item derivation occurs in accordance with a protocol that characterizes the step or steps in the derivation. Protocols are listed in a protocol table 428. Each item derivation is performed by an employee listed in employee table 432.

Unused chips are listed in a chip table 422. Hybridized chips (i.e., chips that have had target applied) are listed in a hybridized chip table 424. A hybridized sample map table 426 lists the relationships between hybridized chips and the samples that have been applied to them.

Stained hybridized chips are scanned in a process referred to here as a scan experiment. Scan experiments are listed in a scan experiment table 430. The scan experiment occurs in accordance with a protocol listed in protocol table 428. The scan experiment is performed by an employee listed in employee table 432.

Figure 4B:
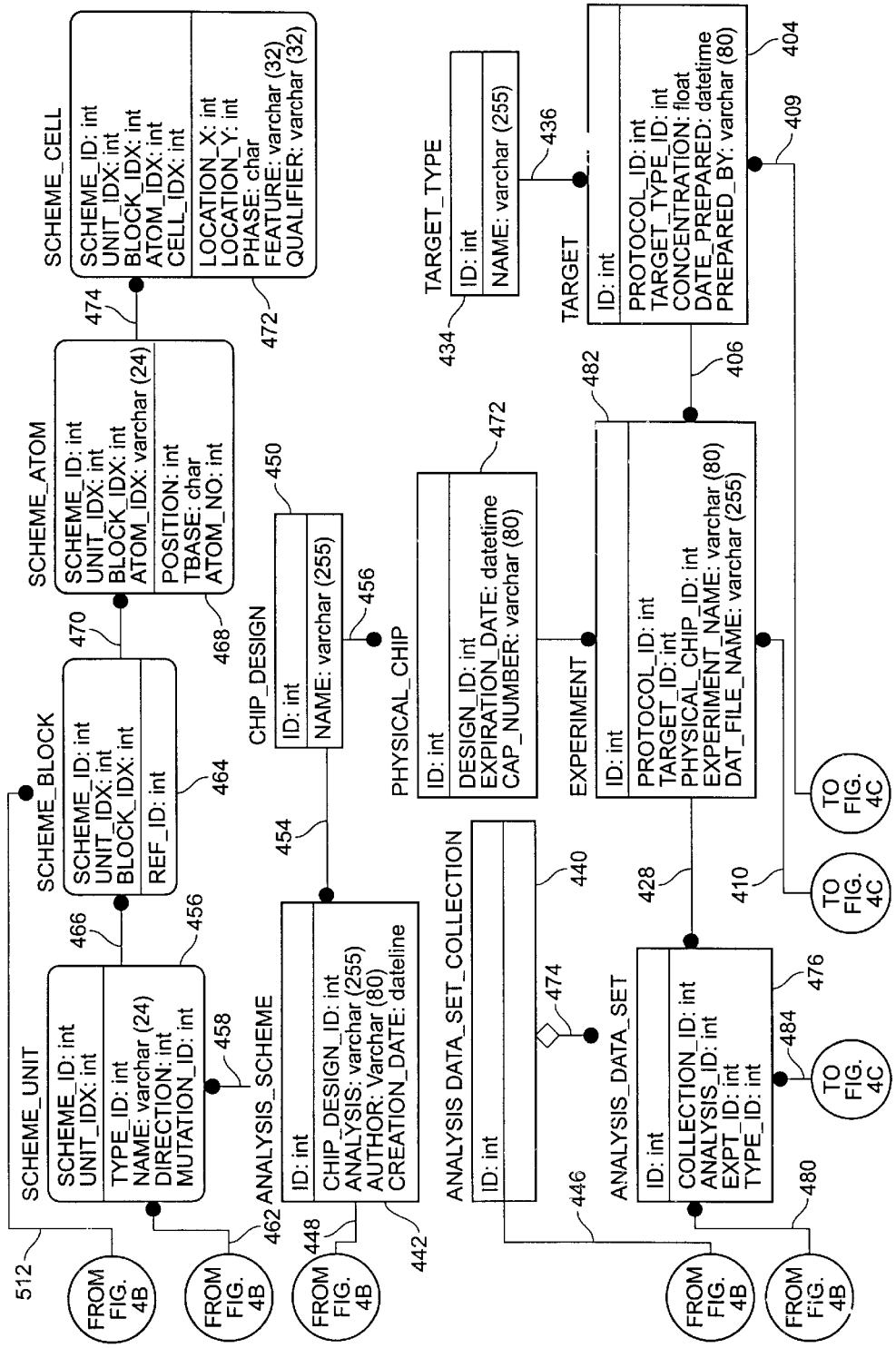

FIG. 4B depicts further details of the data model for items and item derivations. The various item types are listed in an item type table 434 and the various item derivation types are listed in an item derivation type table 436. The relationships between successive item types, e.g., sample and target are defined in an item type derivation table 438. An item has associated attributes. For example, for a target, database 102 may store the concentration, volume, location and/or remaining amount. All item attributes are stored in an item attribute table 440. Item attributes may be shared among multiple items. For example, a series of targets may all share a preparation date. An item attribute item map table 442 implements a many-to-many relationship between item attributes and items. The various types of item attributes such as preparer, preparation date, etc. are listed in an item attribute type table 444. Each item type has corresponding attribute types. Some attribute types are, however, shared among various item types. Accordingly, there is a many-to-many relationship among item attribute types and item types that is implemented by an item type map table 446.

The tables of FIG. 4B represent a powerfully general model of the sample preparation process. Changes in process steps that require changes in the type of information that should be stored may be implemented by changing and adding table contents rather than providing new tables or changing relationships among tables.

Figure 4C:
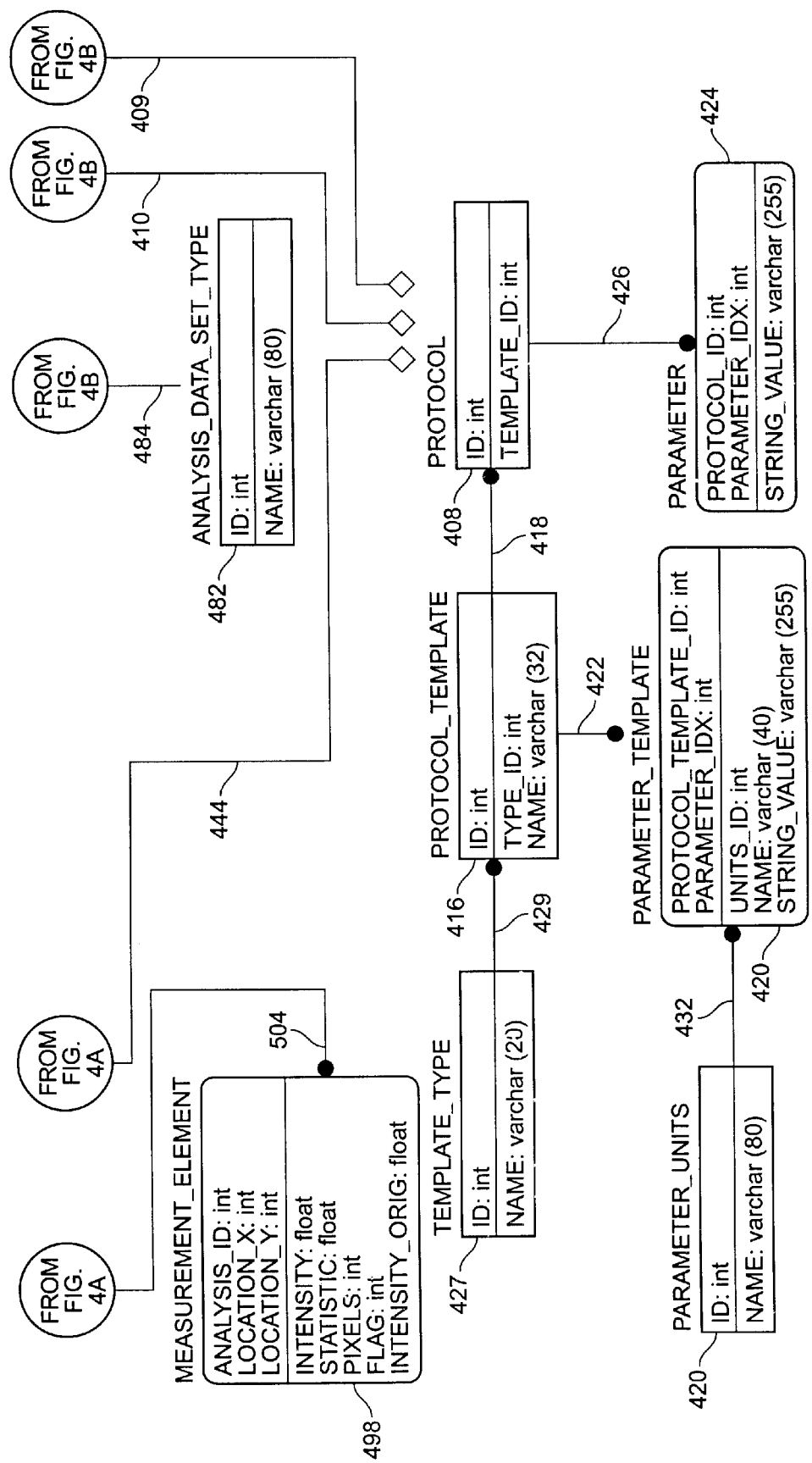

FIG. 4C depicts a detailed data model for storing information about protocols according to the present invention. Protocols as stored in protocol table 428 represent information about particular processes that have been performed including item derivations, analyses, and scan experiments. Each protocol has an associated protocol template. Protocol templates identify protocol types. For example, one protocol template may be a PCR template. All protocols associated with the PCR template identify parameters for performing a PCR procedure. Protocol templates are listed in a protocol template table 448. A parameter table 450 lists all the parameters and their values for all the protocols listed in protocol table 428. A parameter template table 452 lists the various parameter types along with default values. An examples of a parameter template would be a PCR reaction temperature. The parameter template would include a default value for this parameter. Parameter table 450 might then list many different PCR reaction temperature values that would be used by many different protocols. If a parameter value has not been modified by the user, it inherits the standard value of the associated parameter template. A parameter template set is a set of parameter templates that are used for a particular purpose, e.g., in association with protocols according to one or more protocol templates. Parameter template sets are listed in a parameter template set table 454. There are different types of parameter template set and these are listed in a parameter template set table 456. A mapping between parameter template sets and protocol templates is defined by a protocol template set map table 458.

Protocol templates may have associated lengthy verbal information about how to perform protocol steps. A protocol template document table 460 stores references to documents that include instructions for performing protocols.

As with the items, the data model for protocols defined by FIG. 4C is highly general and allows significant changes in the way item derivations, analyses, and experiments are performed without changing the underlying data model.

Referring again to FIG. 4A, there are tables to record information concerning the use of primers in PCR. A fragment table 462 lists all the sequence fragments investigated in conjunction with database 102. Associated with each fragment are one or more primer pairs used to amplify the fragment in a PCR process. A primer pair table 464 lists all the primer pairs including information about whether the primer pair actually worked to amplify the fragment. In order to develop the information about the effectiveness of primer pairs, there is a PCR table 466 that lists records identifying the outcome of multiple PCR operations. The individual PCR operations are identified by reference to item derivation table 420.

A single PCR operation may be used to amplify many different fragments and thus employ many different primer pairs. Of course, a single primer pair may be used in multiple PCR operations. There is therefore a many-to-many relationship between PCR operations and primer pairs that is recorded by a primer pair PCR map table 468.

Information about individual primers is stored in a primer table 470. Also, each primer has an associated protocol in protocol table 428 that characterizes the primer preparation process. Information about primer orders is listed in a primer order table 472. Each primer order is to a vendor and the vendors are listed in a vendor table 474. Each primer order is made by an employee listed in employee table 432. A primer order design map table 476 implements a many-to-many relationship between primer orders and primers.

The data model described here thus preserves information about primers used in PCR reactions. One can improve results by using primers that have successfully amplified a given fragment in the past. Sometimes particular groups of primer pairs cannot be multiplexed together in the same PCR process. The information preserved here thus permits experimenters to make optimal use of expensive and time consuming PCR procedures.

It is also useful to preserve information about the chip production process and the origin of individual chips. A wafer table 478 lists wafers. When chips are produced, many chips are produced at the same time as part of a single wafer. Chip table 422 stores references to wafer table 478 for each chip and the location of each chip on its wafer at production time. Sometimes there is analytic significance associated with the location of a chip on the wafer. Each wafer is produced as part of a lot and the identify of the lot for each wafer is recorded by wafer table 478 as a reference to a lot table 480 that lists each lot.

Figure 4D:
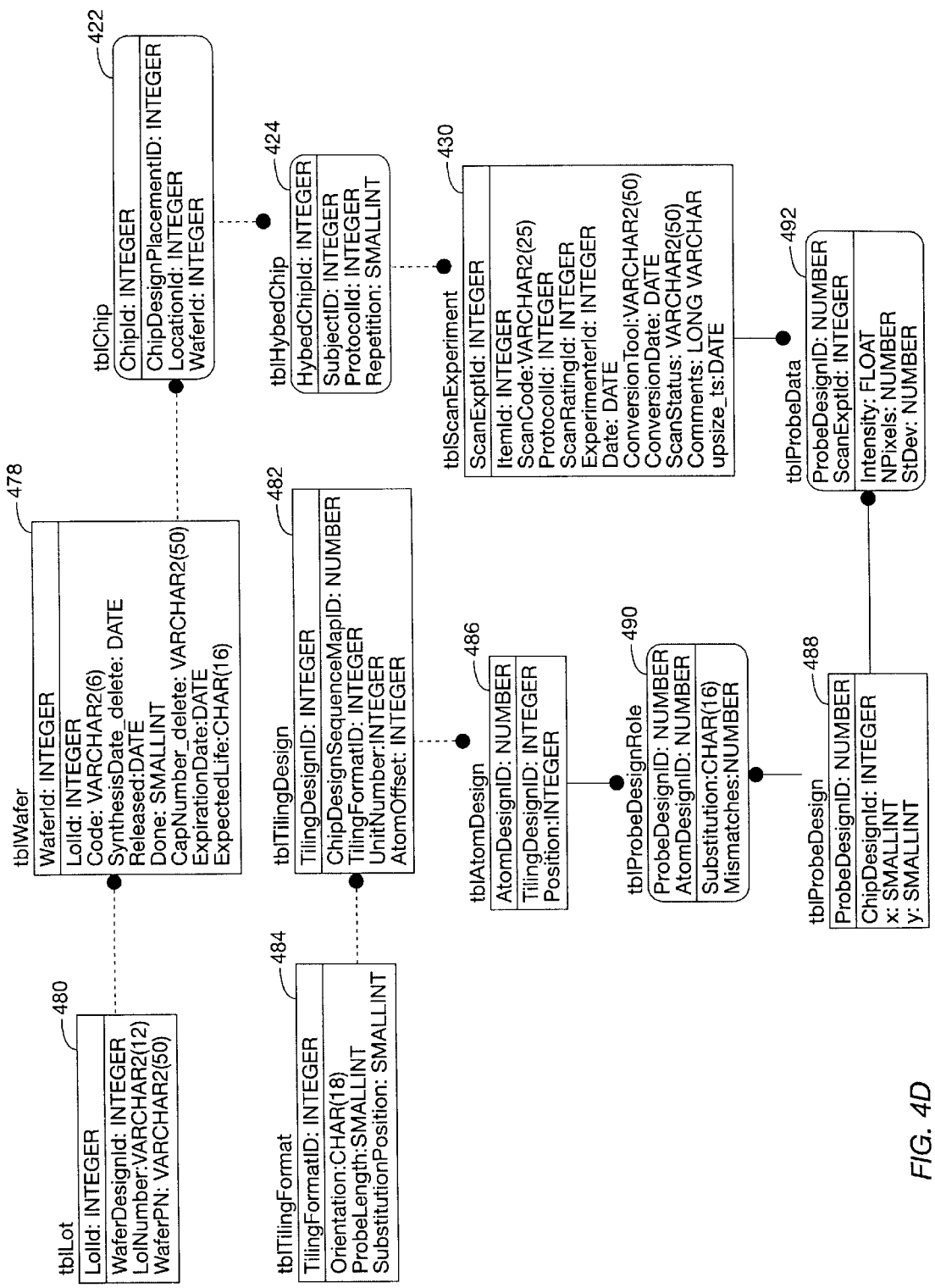

FIG. 4D depicts further details of tables pertaining to chip design that are preferably maintained within polymorphism database 102 according to one embodiment of the present invention. A tiling design table 482 lists tiling designs. Each tiling design represents the application of a particular tiling format to a sequence to be investigated. Tiling formats indicate probe orientation, probe length, and the position within a probe of a single nucleotide polymorphism being investigated. In a preferred embodiment, there may be very few tiling formats and they are listed in a tiling format table 484.

A particular tiling design includes many atom designs specifying the design of a single atom. In one embodiment, an atom is a group of typically four probes used to investigate a single base position with each probe hybridizing to a sequence including a different base at that position. Atom designs are listed in an atom design table 486. Records identifying the designs of individual probes are listed in a probe design table 488. A probe design role table 490 indicates the roles of probes listed in probe design table 488 in the atom designs of atom design table 486. For combinations of probe design and atom design, probe design role table 490 indicates which base the probe hybridizes to at the substitution position and whether the probe represents a match or a mismatch to the wild type.

A probe data table 492 gives the hybridization intensity values for particular probes designs as determined in particular scan experiments. Each record of the table also gives the number of pixels used to determine the intensity value and the standard deviation of intensity as measured among the pixels.

Figure 4E:
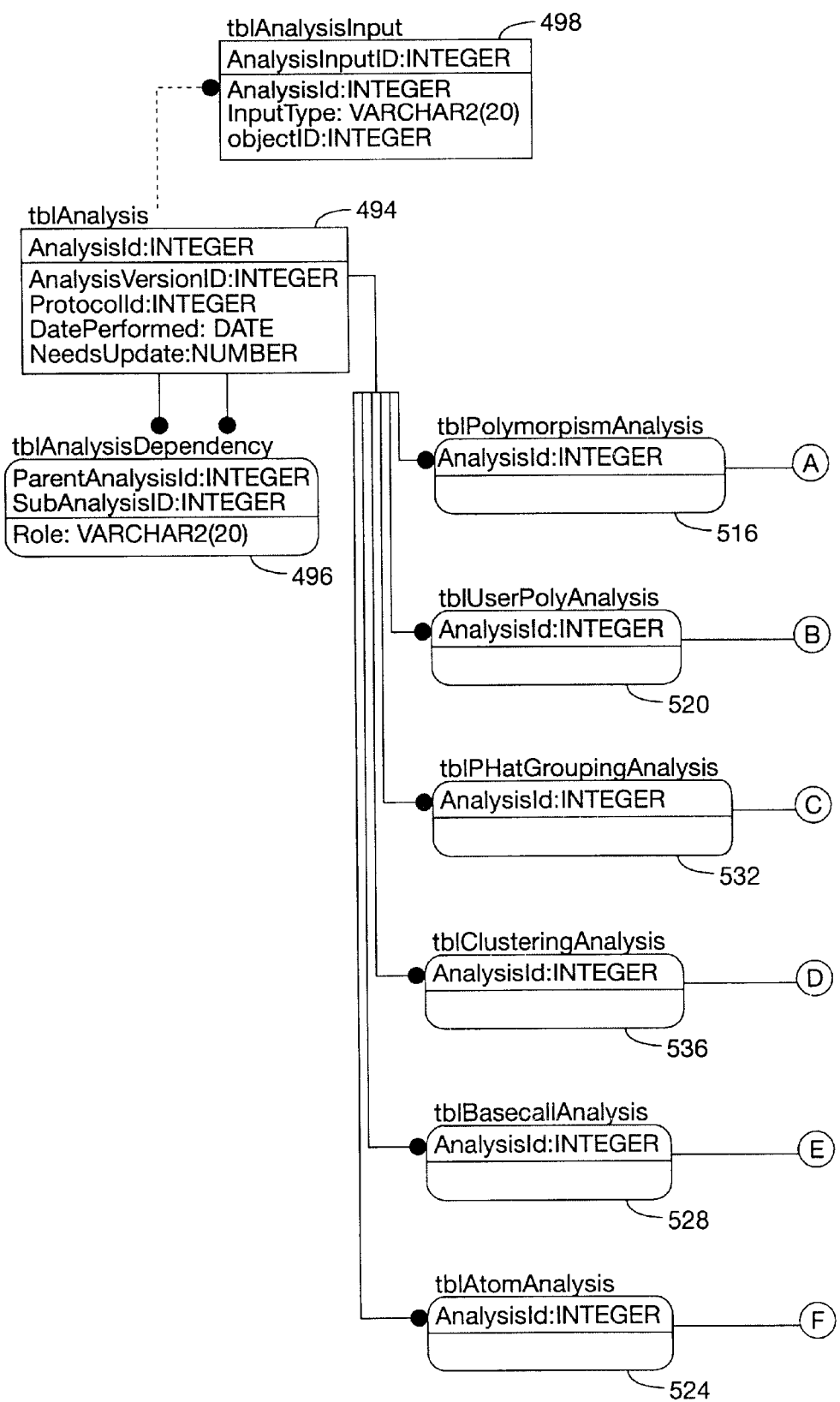
Figure 4E:
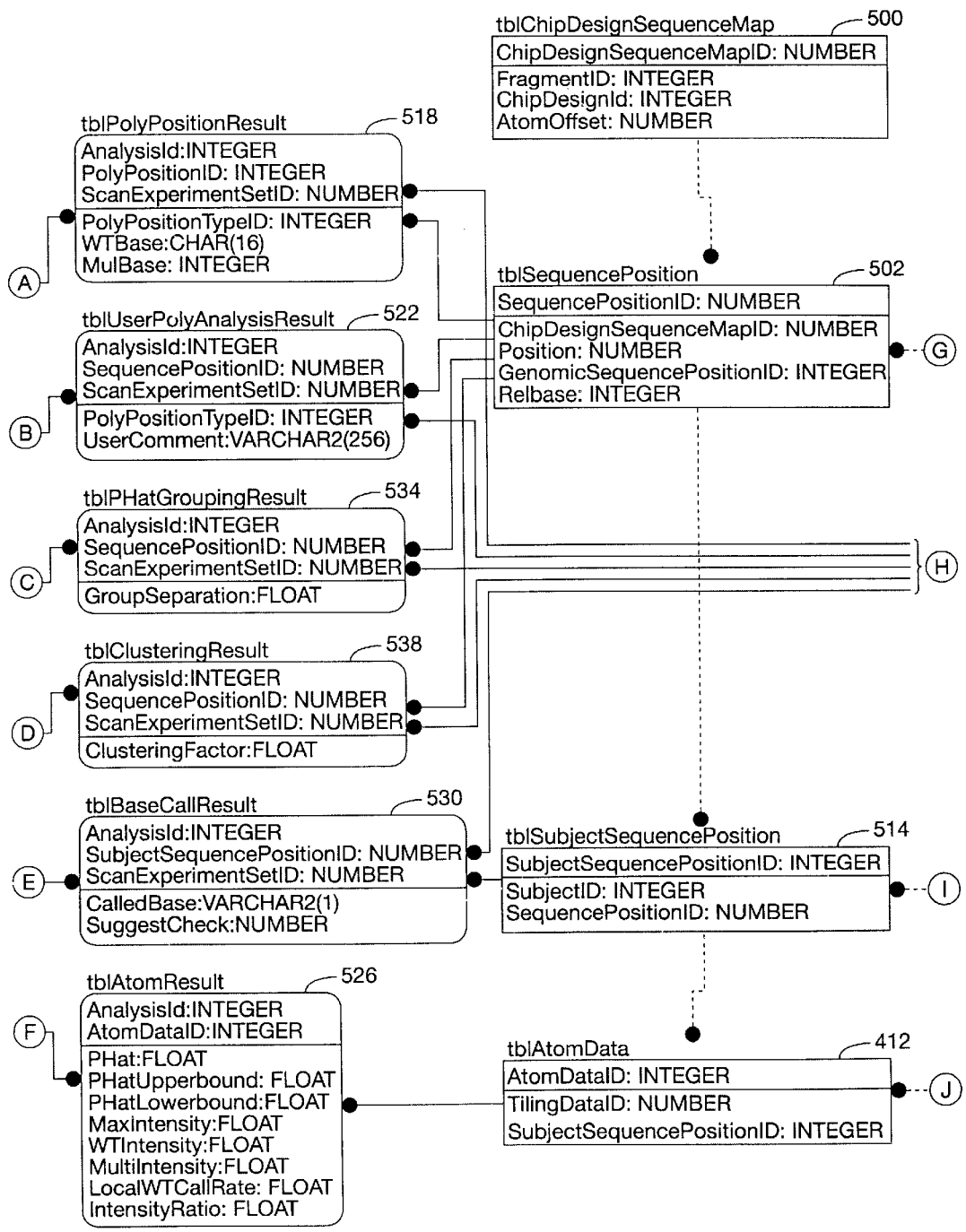
Figure 4E:
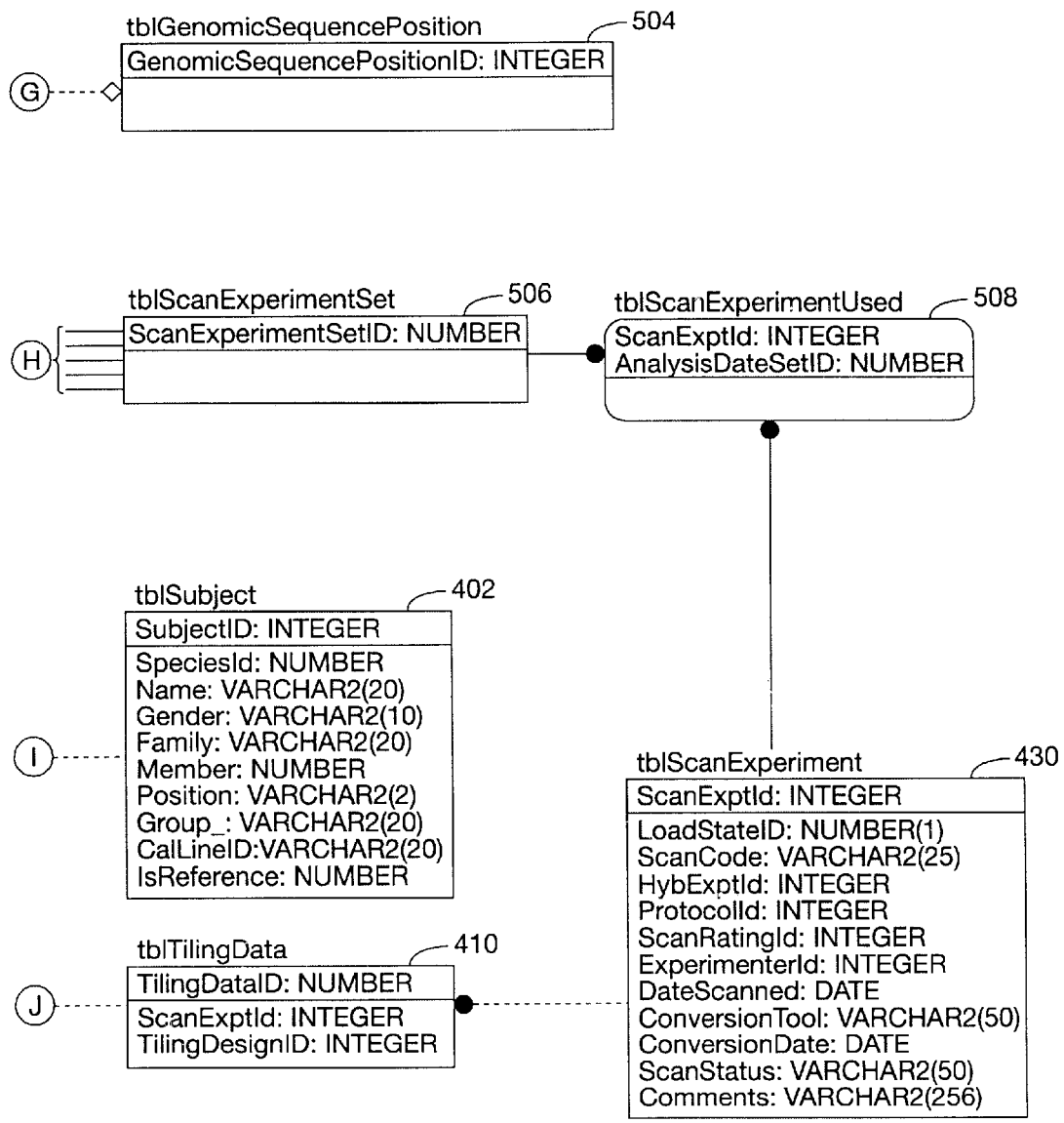
Figure 4F:
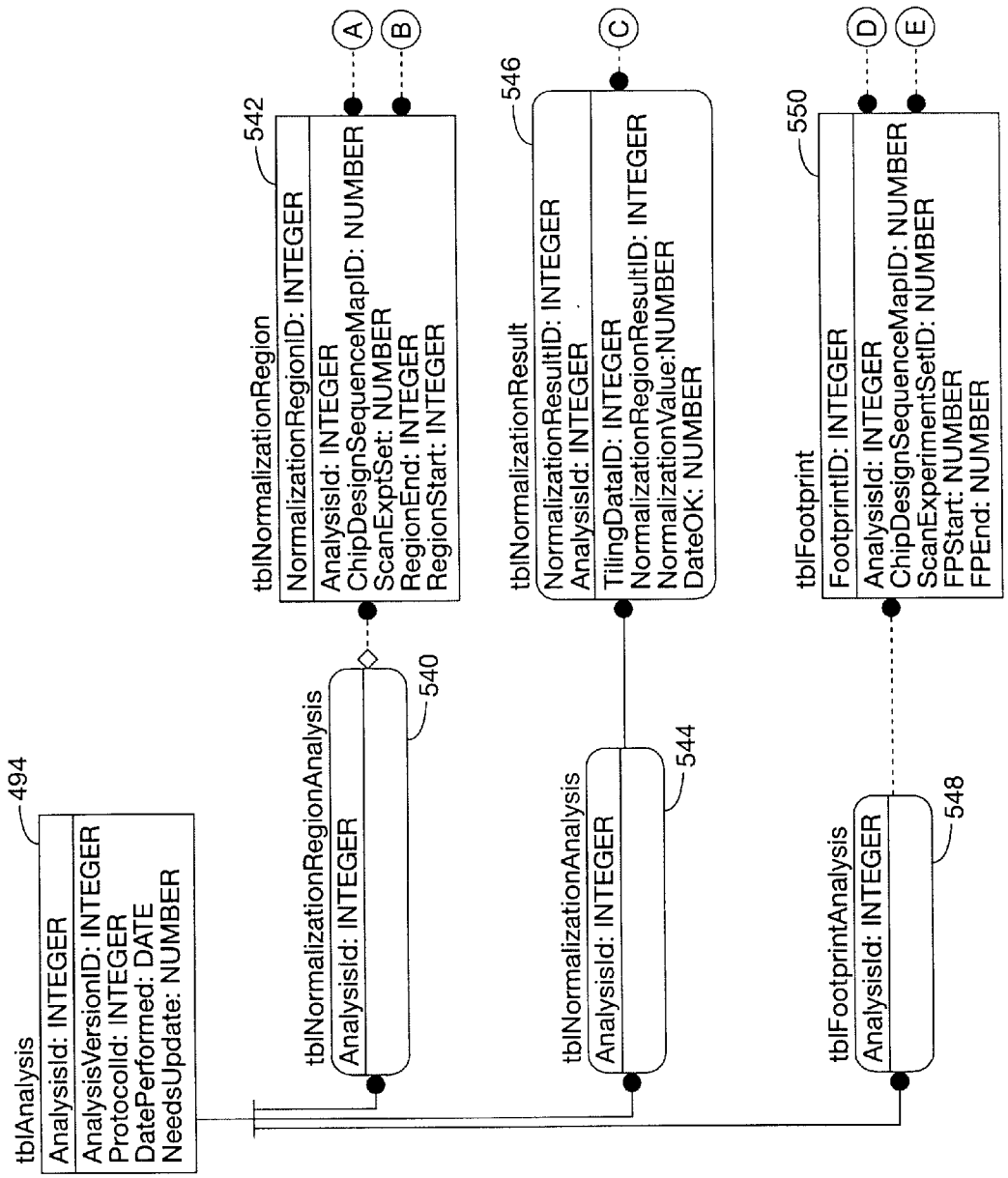
Figure 4F:
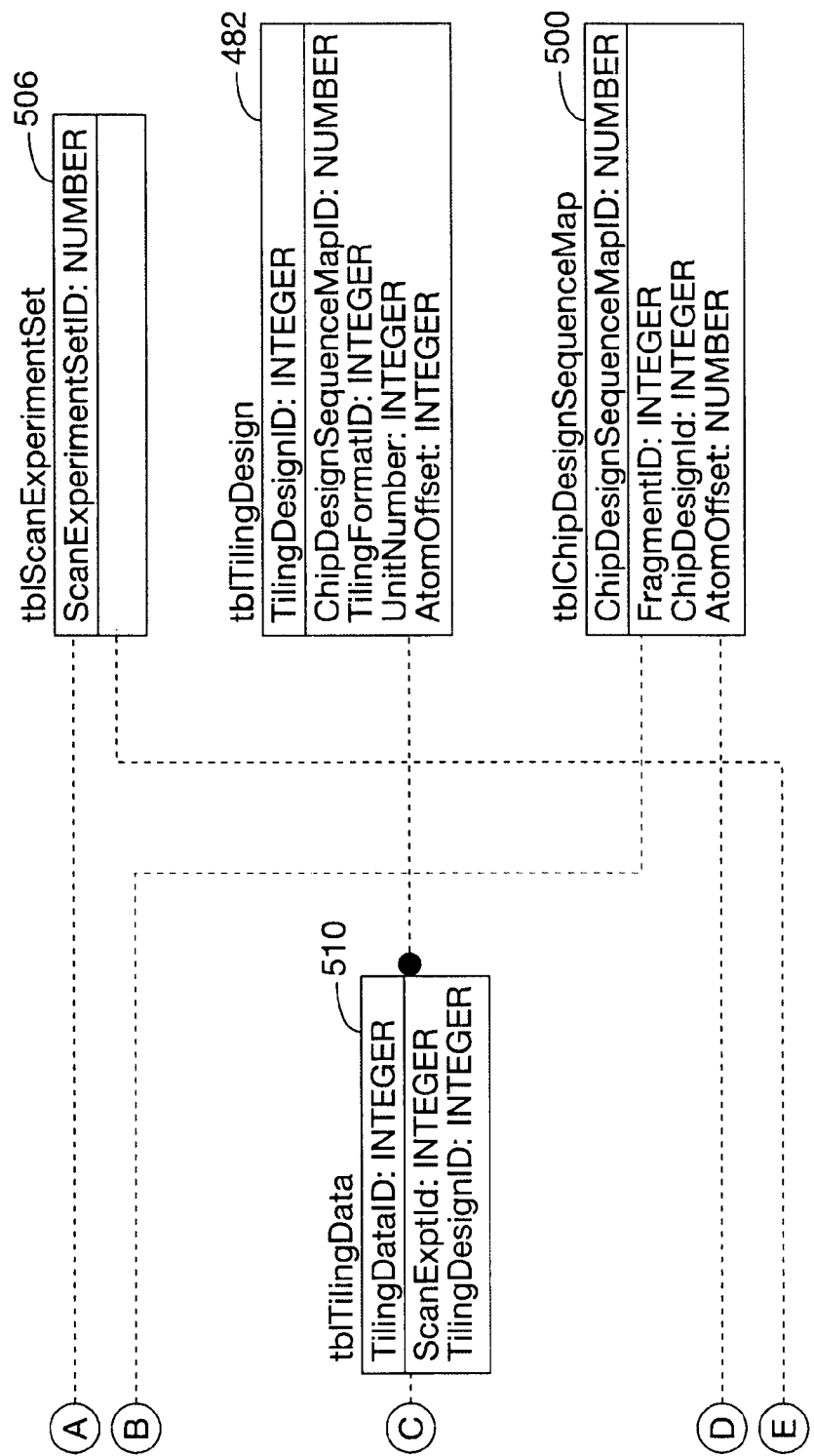
Figure 4G:
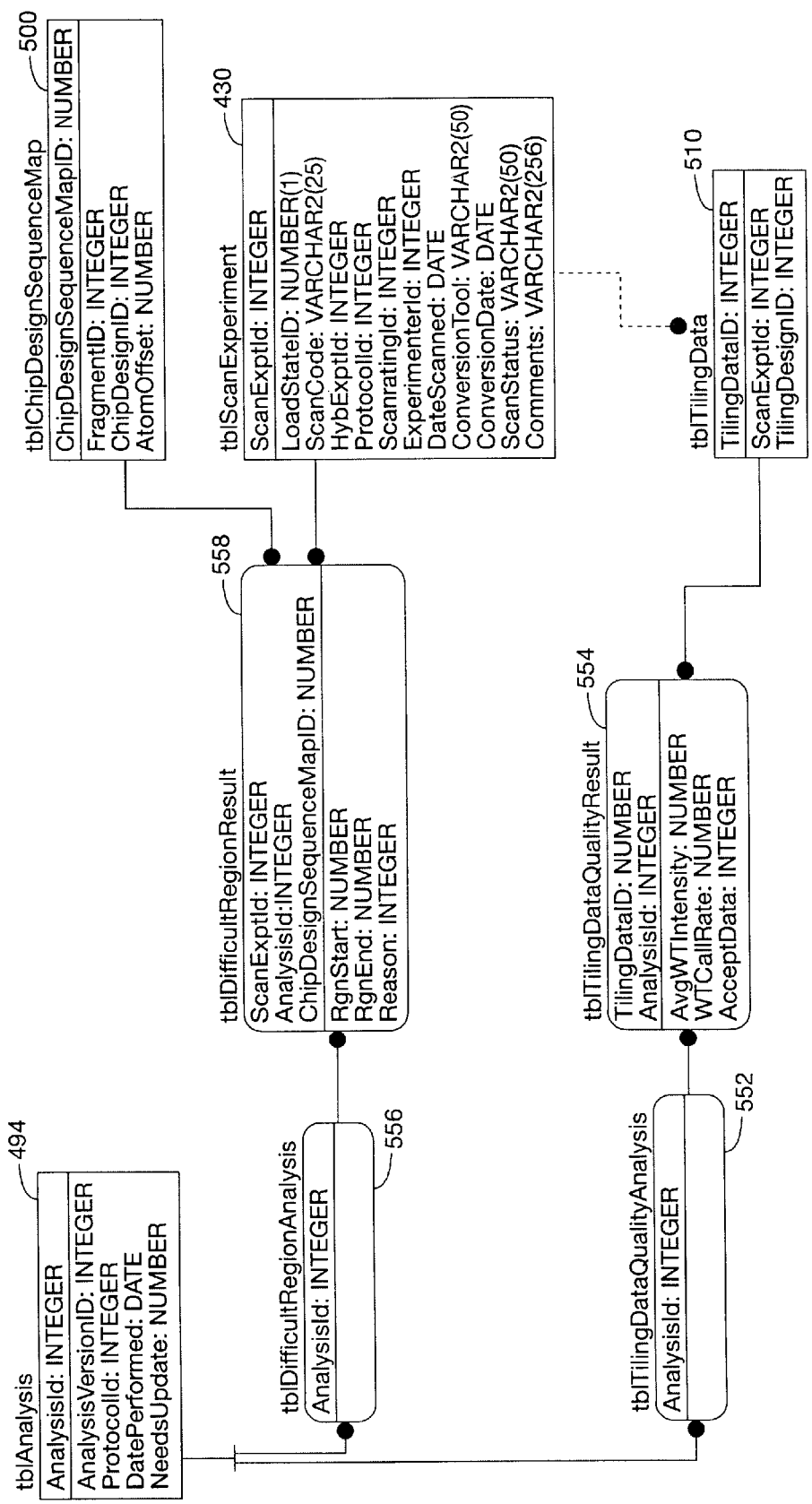

FIGS. 4E–4G depict aspects of polymorphism database 102 related to analysis procedures and their results according to one embodiment of the present invention. An analysis table 494 lists analyses performed. An analysis generally refers to a non-trivial transformation of data. Records of analysis table 494 include references to protocol table 428 to specify parameters used for each analysis. Analyses may take as their input raw data or the results of previous analyses. An analysis dependency table 496 lists dependencies among analyses where one analysis depends on the data developed by another analysis. An analysis input table 498 lists inputs for analyses listed in analysis table 494.

On the right side of FIG. 4E are various tables used to support analyses. A chip design sequence map table 500 correlates particular fragments with chip designs. A sequence position table 502 lists investigated sequence positions indicating their positions on a fragment. Records of sequence position table 502 reference a genomic sequence position table 504 which gives sequence positions in the genome rather than within individual fragments.

A scan experiment set table 506 lists sets of scan experiments. This allows for groupings of experiments for individuals or populations to serve as the basis for polymorphism analysis. A scan experiment used table 508 lists records indicating memberships of a scan experiment in a scan experiment set.

A tiling data table 510 lists records identifying tiling designs as implemented in particular chips measured by particular scan experiments. An atom data table 512 lists the intensities measured for particular sequence positions as measured in scan experiments identified by the tiling data records. A subject sequence position data table 514 lists combinations of sequence position and scan experiment.

A series of tables in FIGS. 4E–4G correspond to different types of analysis that occur during the course of a polymorphism investigation. The types presented here are merely representative. A parallel series of tables provide the analysis results. A polymorphism analysis table 516 lists references to analysis table 494. The results of the performed polymorphism analyses are listed in a polymorphism position result table 518. A record of this table gives a result for a polymorphism analysis for a particular position as determined based on a particular set of scan experiments. In one embodiment the result is whether a particular mutation is certain, likely, possible, or not possible at the position. The result may also be that the reference is wrong.

A user polymorphism analysis table 520 lists user interpretations of results as listed in polymorphism position result table 518. The records of user polymorphism analysis table 520 are references to analysis table 494. The user interpretations themselves are stored in a user polymorphism analysis result table 522. Each result is a likelihood of a particular mutation at a position as considered by a user plus an accompanying user comment.

A P-Hat analysis estimates the relative concentrations of wild type sequence and sequence having a particular mutation as determined in a particular scan experiment. A P-Hat analysis table 524 lists references to analysis table 494. An atom result table 526 gives estimates of the relative concentration along with upper and lower bounds and a maximum intensity. For heterozygous mutations, the estimates of relative concentration will cluster around 0.5 For homozygous mutations, the estimates should cluster around 1.0.

Base call analyses are determinations of the base at a particular position for a particular individual that may be based on more than one experiments. A base call analysis table 528 lists references to analysis table 494. A base call result table 530 lists the called bases for particular combinations of sequence position and subject.

A P-Hat grouping analysis determines a measure of likelihood that data in a set of scan experiments results from separate genotypes. P-hat grouping analyses are listed in a p-hat grouping analysis table 532 by reference to analysis table 494. P-hat grouping analysis results are listed in a mutation fraction result table 534. A group separation is given for various combinations of sequence position and scan experiment set.

A clustering analysis determines an alternative measure of likelihood that data in a set of scan experiments results from separate genotypes. Clustering analyses are listed in a clustering analysis table 536 by reference to analysis table 494. Clustering analysis results are listed in a clustering result table 538. A clustering factor is given for various combinations of sequence position and scan experiment set.

FIG. 4F shows tables which support normalization and footprint finding operations that support the analyses referred to in FIG. 4E. Hybridization intensity measurements made in scan experiments should be normalized over a set of scan experiments. The normalization should take into account differences in amplification level produced by different PCR processes.

Normalization is done by region of sequence. A normalization region analysis determines the boundaries of a region to be normalized. The determination of boundaries takes into account that different fragments of sequence are amplified by different PCR procedures. A normalization region analysis table 540 lists normalization region analyses by reference to analysis table 494. A normalization region result table 542 lists the boundaries for each determined normalization region.

Normalization values for identified normalization regions are themselves determined by normalization analyses. Normalization analyses are listed in a normalization analysis table 544 by reference to analysis table 494. A normalization result table 546 lists the normalization values for regions.

A footprint analysis determines regions of sequence for which the hybridization intensity is elevated for the purposes of quality control. Footprint analyses are listed in a footprint analysis table 548 by reference to analysis table 494. Footprints are identified by sequence starting point and ending point in a particular scan experiment in a footprint table 550.

FIG. 4G depicts tables pertaining to measurement quality according to one embodiment of the present invention. A tiling data quality analysis determines the quality of results from a scan experiment. These analyses are listed in a tiling data quality analysis table 552 by reference to analysis table 494. Tiling data quality analysis results are listed in a tiling data quality result table 554. The results include an average hybridization intensity value for perfect match or mismatch probes. A wild type call rate gives the fraction of atom data where the probe corresponding to the reference base has the highest hybridization intensity. A wild type call rate of around 1.0 indicates good quality. Where the call rate is less than 0.75, the scan experiment should be rejected. An accept data field indicates whether the analysis indicates rejection or acceptance.

Where scan experiment measurements indicate two or more non-wild type bases within a probe length, this indicates a measurement problem for the affected region of sequence. These regions are identified by difficult region analyses listed in a difficult region analysis table 556 by reference to analysis table 494. A difficult region result table 558 lists the regions identified as being difficult.

Analysis dependency table 496 indicates interrelationships among the various analyses of FIGS. 4E–4G. A footprint analysis may depend on a normalization analysis which may in turn depend on a normalization region analysis. A basecall analysis or PHatGrouping analysis may depend on an atom analysis. A polymorphism analysis may depend on any of these analyses and/or a user polymorphism analysis and/or a clustering analysis.

Figure 4H:
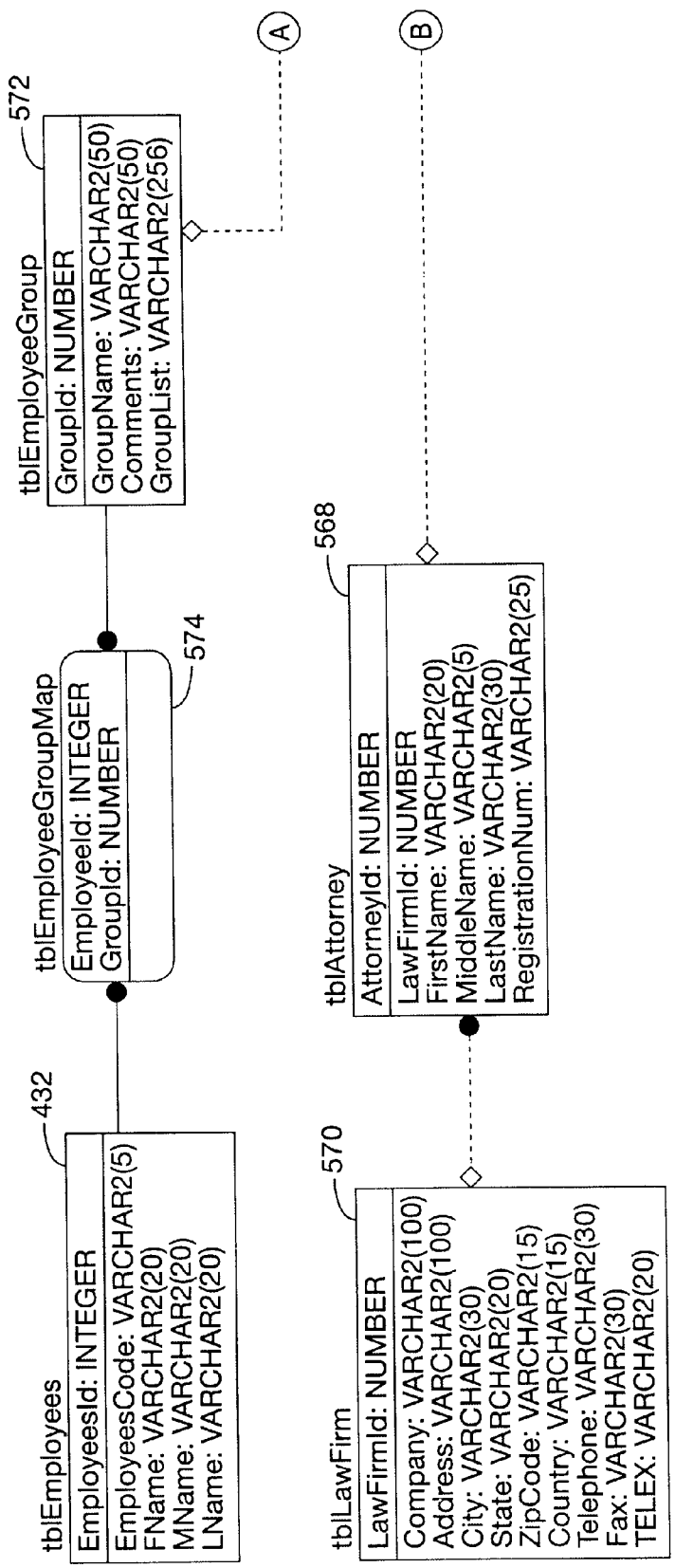
Figure 4H:
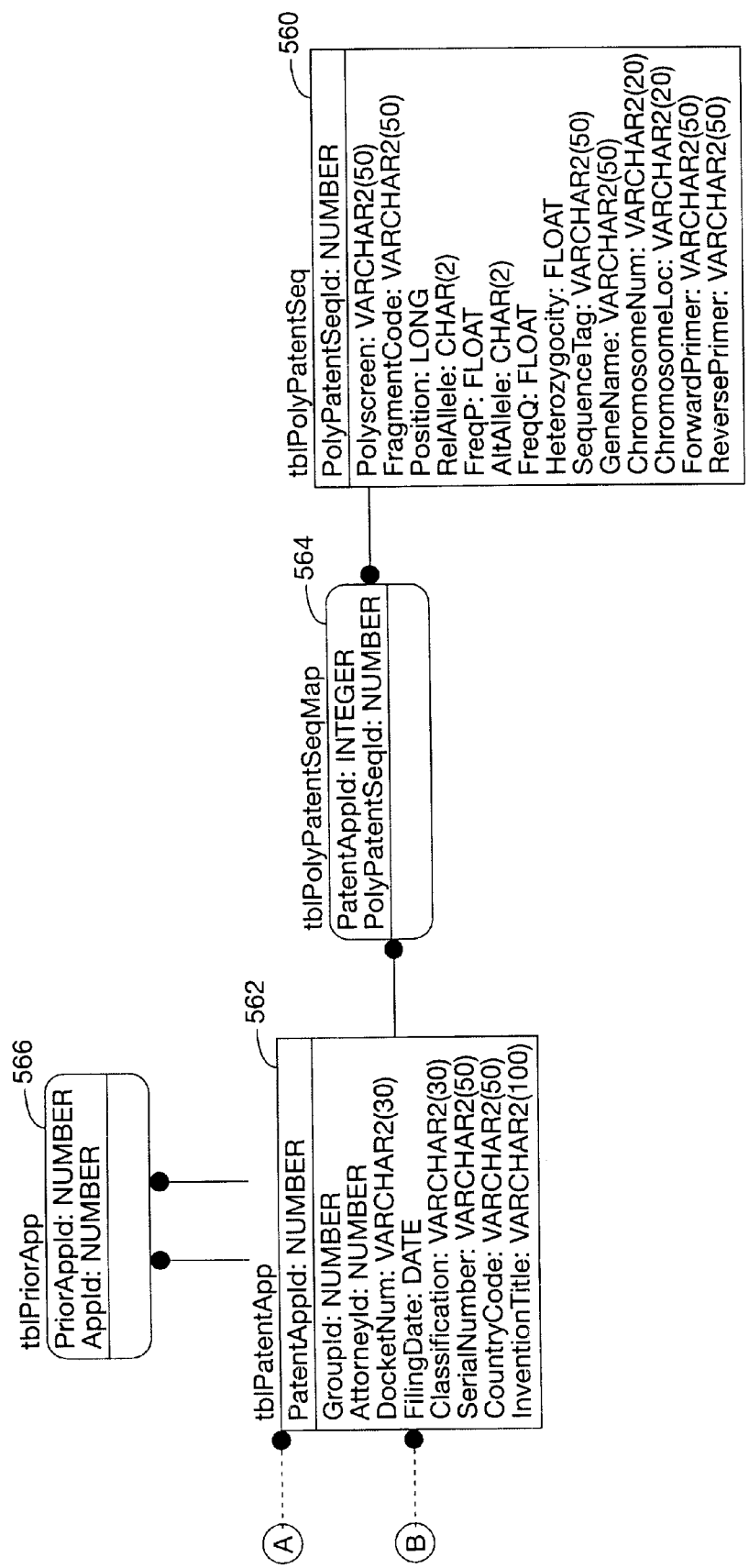

Another aspect of the investigation of polymorphisms is seeking patent protection for identified polymorphisms. FIG. 4H shows tables of polymorphism database 102 related to efforts to seek patent protection according to one embodiment of the present invention. A polymorphism patent sequence table 560 lists sequences for which patent protection is sought. A patent application table 562 lists patent applications directed toward the protection of polymorphisms. A polymer patent application sequence map table 564 implements a many-to-many relationship between patent applications and sequences. A prior application table 566 lists relationships between patent applications and prior related patent applications. An attorney table 568 lists attorneys responsible for preparing patent applications listed in patent application table 562. A law firm table 570 lists the law firms to which the attorneys listed in attorney table 568 belong.

An employee group table 572 lists groups of inventors for the patent applications listed in table 562. Individual inventors are listed in employee table 432. An employee group map table 574 implements a many-to-many relationship between inventors and groups of inventors.

The data model of FIG. 4H greatly facilitates the process of securing patent protection for polymorphisms and thereby increases the commercial incentive for investigation of polymorphisms.

What is claimed is:

1. A computer program embodied on a computer-readable medium comprising:
   an item table listing a plurality of item records identifying items, wherein said item records are used in a biological analysis;
   an item attribute table listing a plurality of item attribute records identifying attributes of said items; and
   wherein an association is defined between a subset of the item records and a plurality of item attribute records.

2. The computer, program of claim 1 wherein said biological analysis comprises a polymorphism analysis.

3. A computer program embodied on a computer-readable storage medium comprising:
   an atom result table listing a plurality of atom result records, specifying relative wild-type and mutant sequence concentrations in targets; and
   a subject sequence position table listing a plurality of subject sequence position records, specifying combinations of subjects from whom said targets are derived and sequence positions, each said atom result record being associated with one or more atom result records.

4. The computer program of claim 3 wherein said atom result records further specify upper and lower bounds for said concentrations.

5. The computer program of claim 3 further comprising:
   one or more instructions for accessing a subject table listing subject records specifying said subjects.

6. A computer program embodied in a computer-readable medium comprising:
   one or more instructions for accessing a polymorphism table listing polymorphism sequence records specifying sequences known to contain polymorphisms; and
   one or more instructions for accessing a patent application table listing patent application records specifying one or more polymorphisms specified by said. polymorphism sequence records.

7. The computer program of claim 6 wherein said polymorphism sequence records specify for each one of said polymorphisms a polymorphism position, a reference allele, and a base allele.

8. The computer program of claim 7 wherein said polymorphism sequence records further specify for each one of said polymorphisms a measured heterozygocity.

9. A method of creating a database in a computer system, the method comprising:
   creating an item table listing a plurality of item records identifying items used in biological analysis; and
   creating an item attribute table listing a plurality of item attribute records identifying attributes of said items; and
   wherein an association is defined between a subset of the item records and a plurality of item attribute records.

10. The method of claim 9 further comprising the step of:
    creating an item attribute item map table defining said association between a subset of the item records and a plurality of item attribute records, said item attribute item map table listing a plurality of map records identifying both a particular item attribute and a particular item.

11. The method of claim 9 comprising:
    an item derivation table listing a plurality of item derivation records identifying transformations between said items used in biological analysis.

12. The method of claim 11 further comprising:

creating a protocol table listing a plurality of protocol records specifying parameters of said transformation.

13. The method of claim 9 wherein said biological analysis comprises a polymorphism analysis.

14. A method for creating data relationships in a computer system, the method comprising:

creating an atom result table listing a plurality of atom result records, specifying relative wild-type and mutant sequence concentrations in targets; and creating a subject sequence position table listing a plurality of subject sequence position records, specifying combinations of subjects from whom said targets are derived and sequence positions, each said atom result record being associated with one or more atom result records.

15. The method of claim 14 wherein said atom result records further specify upper and lower bounds for said concentrations.

16. The method of claim 14 further comprising:

creating a subject table listing subject records specifying said subjects.

17. A method for creating data relationships in a computer system, the method comprising:

creating a polymorphism table listing polymorphism sequence records specifying sequences known to contain polymorphisms; and creating a patent application table listing patent application records specifying one or more polymorphisms specified by said polymorphism sequence records.

18. The method of claim 17, wherein said polymorphism sequence records specify for each one of said polymorphisms a polymorphism position, a reference allele, and a base allele.

19. The method of claim 18, wherein said polymorphism sequence records further specify for at least one of said polymorphisms a measured heterozygocity.

* * * * *